US008398626B2

(12) United States Patent
Buysse et al.

(10) Patent No.: US 8,398,626 B2
(45) Date of Patent: *Mar. 19, 2013

(54) ELECTROSURGICAL SYSTEM EMPLOYING MULTIPLE ELECTRODES

(75) Inventors: Steven P. Buysse, Niwot, CO (US); Gary Dobbins, Longmont, CO (US); Brandon Gay, Superior, CO (US); David N. Heard, Boulder, CO (US); James W. McPherson, Boulder, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/298,461

(22) Filed: Nov. 17, 2011

(65) Prior Publication Data

US 2012/0059367 A1    Mar. 8, 2012

Related U.S. Application Data

(63) Continuation of application No. 12/748,582, filed on Mar. 29, 2010, now Pat. No. 8,062,290, which is a continuation of application No. 12/201,291, filed on Aug. 29, 2008, now Pat. No. 7,699,842, which is a continuation of application No. 11/242,391, filed on Oct. 3, 2005, now Pat. No. 7,553,309.

(60) Provisional application No. 60/616,971, filed on Oct. 8, 2004.

(51) Int. Cl.
*A61B 18/12* (2006.01)

(52) U.S. Cl. ........................................................ 606/34

(58) Field of Classification Search .............. 606/32–35, 606/37–42, 44–52
See application file for complete search history.

(56) References Cited

U.S. PATENT DOCUMENTS

| | | |
|---|---|---|
| 2,031,682 A | 2/1936 | Frederick et al. |
| D223,367 S | 4/1972 | Kountz |
| 4,074,718 A | 2/1978 | Morrison, Jr. et al. |
| D263,020 S | 2/1982 | Rau, III |
| D266,842 S | 11/1982 | Villers et al. |
| 4,375,220 A | 3/1983 | Matvias |
| 4,411,266 A | 10/1983 | Cosman |
| D278,306 S | 4/1985 | McIntosh |
| 4,565,200 A | 1/1986 | Cosman |
| 4,576,177 A | 3/1986 | Webster, Jr. |
| 4,608,977 A | 9/1986 | Brown |
| 4,662,383 A | 5/1987 | Sogawa et al. |
| 4,739,759 A | 4/1988 | Rexroth et al. |
| D295,893 S | 5/1988 | Sharkany et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Michael Peffley
*Assistant Examiner* — Ronald Hupczey, Jr.

(57) ABSTRACT

A system for heat ablation of tissue, the system comprising a radiofrequency source configured to supply RF energy to at least two electrodes for treating tissue, at least one return electrode configured to return the RF energy to the radiofrequency source, a controller configured to sequentially apply the RF energy to each of the at least two electrodes for a pre-determinable period of time and circuitry configured to switch the RF energy to an internal load. The RF energy is applied simultaneously to the internal load and at least one of the at least two electrodes. The controller is configured to apply the RF energy to the next electrode in the sequence when the amount of time the applied RF energy is off is greater than a predetermined minimum off time.

15 Claims, 7 Drawing Sheets

U.S. PATENT DOCUMENTS

| | | | |
|---|---|---|---|
| D295,894 S | 5/1988 | Sharkany et al. |
| 4,832,024 A | 5/1989 | Boussignac et al. |
| 4,880,719 A | 11/1989 | Murofushi et al. |
| 4,961,435 A | 10/1990 | Kitagawa et al. |
| 4,966,597 A | 10/1990 | Cosman |
| 4,993,430 A | 2/1991 | Shimoyama et al. |
| 5,029,588 A | 7/1991 | Yock et al. |
| 5,103,804 A | 4/1992 | Abele et al. |
| 5,225,741 A | 7/1993 | Auld et al. |
| 5,230,623 A | 7/1993 | Guthrie et al. |
| 5,233,515 A | 8/1993 | Cosman |
| 5,246,438 A | 9/1993 | Langberg |
| 5,267,994 A | 12/1993 | Gentelia et al. |
| 5,281,213 A | 1/1994 | Milder et al. |
| 5,323,778 A | 6/1994 | Kandarpa et al. |
| 5,330,470 A | 7/1994 | Hagen |
| 5,330,518 A | 7/1994 | Nielson et al. |
| 5,334,193 A | 8/1994 | Nardella |
| 5,342,357 A | 8/1994 | Nardella |
| 5,348,554 A | 9/1994 | Imran et al. |
| 5,370,675 A | 12/1994 | Edwards et al. |
| D354,218 S | 1/1995 | Van de Peer |
| 5,383,876 A | 1/1995 | Nardella |
| 5,383,917 A | 1/1995 | Desai et al. |
| 5,385,148 A | 1/1995 | Lesh et al. |
| 5,403,311 A | 4/1995 | Abele et al. |
| 5,409,000 A | 4/1995 | Imran |
| 5,409,006 A | 4/1995 | Buchholtz et al. |
| 5,417,686 A | 5/1995 | Peterson et al. |
| 5,433,739 A | 7/1995 | Sluijter et al. |
| 5,437,662 A | 8/1995 | Nardella |
| 5,458,597 A | 10/1995 | Edwards et al. |
| 5,462,521 A | 10/1995 | Brucker et al. |
| 5,472,441 A | 12/1995 | Edwards et al. |
| 5,490,850 A | 2/1996 | Ellman et al. |
| 5,500,012 A | 3/1996 | Brucker et al. |
| 5,520,684 A | 5/1996 | Imran |
| 5,536,267 A | 7/1996 | Edwards et al. |
| 5,571,147 A | 11/1996 | Sluijter et al. |
| 5,588,432 A | 12/1996 | Crowley |
| 5,599,345 A | 2/1997 | Edwards et al. |
| 5,643,197 A | 7/1997 | Brucker et al. |
| 5,647,871 A | 7/1997 | Levine et al. |
| 5,662,111 A | 9/1997 | Cosman |
| 5,688,267 A | 11/1997 | Panescu et al. |
| 5,735,847 A | 4/1998 | Gough et al. |
| 5,775,338 A | 7/1998 | Hastings |
| 5,792,146 A | 8/1998 | Cosman |
| 5,848,967 A | 12/1998 | Cosman |
| 5,849,011 A | 12/1998 | Jones et al. |
| 5,868,740 A | 2/1999 | LeVeen et al. |
| 5,921,982 A | 7/1999 | Lesh et al. |
| 5,943,719 A | 8/1999 | Feldman et al. |
| 5,951,546 A | 9/1999 | Lorentzen |
| 6,001,093 A | 12/1999 | Swanson et al. |
| 6,006,126 A | 12/1999 | Cosman |
| 6,053,912 A | 4/2000 | Panescu et al. |
| D424,693 S | 5/2000 | Pruter |
| D424,694 S | 5/2000 | Tetzlaff et al. |
| D425,201 S | 5/2000 | Tetzlaff et al. |
| 6,059,780 A | 5/2000 | Gough et al. |
| 6,061,551 A | 5/2000 | Sorrells et al. |
| 6,074,389 A | 6/2000 | Levine et al. |
| 6,080,149 A | 6/2000 | Huang et al. |
| 6,106,524 A | 8/2000 | Eggers et al. |
| 6,132,426 A | 10/2000 | Kroll |
| 6,146,380 A | 11/2000 | Racz et al. |
| 6,162,216 A | 12/2000 | Guziak et al. |
| 6,203,541 B1 | 3/2001 | Keppel |
| 6,241,725 B1 | 6/2001 | Cosman |
| 6,246,912 B1 | 6/2001 | Sluijter et al. |
| 6,287,305 B1 | 9/2001 | Heim et al. |
| D449,886 S | 10/2001 | Tetzlaff et al. |
| 6,306,132 B1 | 10/2001 | Moorman et al. |
| 6,337,998 B1 | 1/2002 | Behl et al. |
| D457,958 S | 5/2002 | Dycus et al. |
| D457,959 S | 5/2002 | Tetzlaff et al. |
| 6,398,779 B1 | 6/2002 | Buysse et al. |
| 6,398,781 B1 | 6/2002 | Goble et al. |
| 6,432,070 B1 | 8/2002 | Talish et al. |
| 6,478,793 B1 | 11/2002 | Cosman et al. |
| 6,500,172 B1 | 12/2002 | Panescu et al. |
| 6,506,189 B1 | 1/2003 | Rittman, III et al. |
| 6,530,922 B2 | 3/2003 | Cosman et al. |
| 6,537,272 B2 | 3/2003 | Christopherson et al. |
| 6,575,969 B1 | 6/2003 | Rittman, III et al. |
| 6,582,427 B1 | 6/2003 | Goble et al. |
| 6,605,085 B1 | 8/2003 | Edwards |
| 6,613,047 B2 | 9/2003 | Edwards |
| 6,629,974 B2 | 10/2003 | Penny et al. |
| 6,673,070 B2 | 1/2004 | Edwards et al. |
| D487,039 S | 2/2004 | Webster et al. |
| 6,685,729 B2 | 2/2004 | Gonzalez |
| 6,723,091 B2 | 4/2004 | Goble et al. |
| D496,997 S | 10/2004 | Dycus et al. |
| D499,181 S | 11/2004 | Dycus et al. |
| 6,918,907 B2 | 7/2005 | Kelly et al. |
| 7,008,421 B2 | 3/2006 | Daniel et al. |
| D525,361 S | 7/2006 | Hushka |
| D531,311 S | 10/2006 | Guerra et al. |
| 7,131,970 B2 | 11/2006 | Moses et al. |
| 7,137,980 B2 | 11/2006 | Buysse et al. |
| D533,942 S | 12/2006 | Kerr et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,169,146 B2 | 1/2007 | Truckai et al. |
| 7,179,255 B2 | 2/2007 | Lettice et al. |
| 7,186,222 B1 | 3/2007 | Callister et al. |
| D541,418 S | 4/2007 | Schechter et al. |
| 7,207,989 B2 | 4/2007 | Pike, Jr. et al. |
| D541,938 S | 5/2007 | Kerr et al |
| 7,218,958 B2 | 5/2007 | Rashidi |
| 7,220,260 B2 | 5/2007 | Fleming et al. |
| 7,235,070 B2 | 6/2007 | Vanney |
| 7,235,073 B2 | 6/2007 | Levine et al. |
| 7,238,184 B2 | 7/2007 | Megerman et al. |
| 7,252,667 B2 | 8/2007 | Moses et al. |
| 7,264,619 B2 | 9/2007 | Venturelli |
| 7,278,991 B2 | 10/2007 | Morris et al. |
| 7,282,049 B2 | 10/2007 | Orszulak et al. |
| 7,294,127 B2 | 11/2007 | Leung et al. |
| 7,294,143 B2 | 11/2007 | Francischelli |
| 7,302,285 B2 | 11/2007 | Fuimaono et al. |
| 7,303,558 B2 | 12/2007 | Swanson |
| 7,331,947 B2 | 2/2008 | McGuckin, Jr. et al. |
| RE40,156 E | 3/2008 | Sharps et al. |
| D564,662 S | 3/2008 | Moses et al. |
| 7,341,586 B2 | 3/2008 | Daniel et al. |
| 7,344,533 B2 | 3/2008 | Pearson et al. |
| 7,364,578 B2 | 4/2008 | Francischelli et al. |
| 7,364,579 B2 | 4/2008 | Mulier et al. |
| 7,367,974 B2 | 5/2008 | Haemmerich et al. |
| 7,367,975 B2 | 5/2008 | Malecki et al. |
| 7,387,625 B2 | 6/2008 | Hovda et al. |
| D576,932 S | 9/2008 | Strehler |
| 7,419,486 B2 | 9/2008 | Kampa |
| 7,419,487 B2 | 9/2008 | Johnson et al. |
| 7,419,488 B2 | 9/2008 | Ciarrocca et al. |
| 7,419,489 B2 | 9/2008 | Vanney et al. |
| 7,422,587 B2 | 9/2008 | Bek et al. |
| 7,480,533 B2 | 1/2009 | Cosman et al. |
| D594,736 S | 6/2009 | Esjunin |
| D594,737 S | 6/2009 | Kelly et al. |
| 7,553,309 B2 | 6/2009 | Buysse et al. |
| D606,203 S | 12/2009 | Husheer et al. |
| D613,412 S | 4/2010 | DeCarlo |
| 7,811,283 B2 | 10/2010 | Moses et al. |
| 7,863,984 B1 | 1/2011 | Behnke |
| D634,010 S | 3/2011 | DeCarlo |
| 8,035,570 B2 | 10/2011 | Prakash et al. |
| 8,038,693 B2 | 10/2011 | Allen |
| 2001/0034518 A1* | 10/2001 | Edwards et al. ............. 606/41 |
| 2002/0111615 A1 | 8/2002 | Cosman et al. |
| 2002/0156472 A1* | 10/2002 | Lee et al. ............. 606/41 |
| 2003/0153908 A1 | 8/2003 | Goble et al. |

| | | |
|---|---|---|
| 2004/0267256 A1 | 12/2004 | Garabedian et al. |
| 2005/0096681 A1 | 5/2005 | Desinger et al. |
| 2005/0155743 A1 | 7/2005 | Getz, Jr. et al. |
| 2006/0079885 A1 | 4/2006 | Rick et al. |
| 2007/0046260 A1 | 3/2007 | Ishikawa |
| 2007/0066971 A1 | 3/2007 | Podhajsky |
| 2007/0073285 A1 | 3/2007 | Peterson |
| 2007/0078453 A1 | 4/2007 | Johnson |
| 2007/0078454 A1 | 4/2007 | McPherson |
| 2007/0258838 A1 | 11/2007 | Drake et al. |
| 2007/0260240 A1 | 11/2007 | Rusin |
| 2008/0021448 A1 | 1/2008 | Orszulak |
| 2008/0027424 A1 | 1/2008 | DeCarlo et al. |
| 2008/0183165 A1 | 7/2008 | Buysse et al. |
| 2008/0287946 A1 | 11/2008 | DeCarlo et al. |
| 2009/0054891 A1 | 2/2009 | Buysse et al. |
| 2009/0234350 A1 | 9/2009 | Behnke et al. |
| 2010/0053015 A1 | 3/2010 | Willyard |
| 2010/0057070 A1 | 3/2010 | Behnke et al. |
| 2010/0076422 A1 | 3/2010 | Podhajsky |
| 2010/0087808 A1 | 4/2010 | Paulus |
| 2010/0092939 A1 | 4/2010 | Belous et al. |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0217251 A1 | 8/2010 | Rossetto et al. |
| 2010/0217252 A1 | 8/2010 | Rossetto et al. |
| 2010/0234839 A1 | 9/2010 | Smith et al. |
| 2010/0256624 A1 | 10/2010 | Brannan |
| 2010/0262134 A1 | 10/2010 | Jensen et al. |
| 2010/0286681 A1 | 11/2010 | Podhajsky |
| 2010/0286682 A1 | 11/2010 | Podhajsky |
| 2010/0286683 A1 | 11/2010 | Podhajsky |
| 2010/0305559 A1 | 12/2010 | Brannan et al. |
| 2010/0305560 A1 | 12/2010 | Peterson |
| 2010/0305561 A1 | 12/2010 | Prakash et al. |
| 2010/0321192 A1 | 12/2010 | Brannan |
| 2010/0321257 A1 | 12/2010 | Brannan |
| 2010/0331834 A1 | 12/2010 | Peterson et al. |
| 2011/0034913 A1 | 2/2011 | Brannan |
| 2011/0034917 A1 | 2/2011 | Brannan |
| 2011/0034919 A1 | 2/2011 | DeCarlo |
| 2011/0040300 A1 | 2/2011 | Brannan |
| 2011/0054458 A1 | 3/2011 | Behnke |
| 2011/0054459 A1 | 3/2011 | Peterson |
| 2011/0060325 A1 | 3/2011 | Bonn |
| 2011/0060326 A1 | 3/2011 | Smith et al. |
| 2011/0066144 A1 | 3/2011 | Bonn et al. |
| 2011/0071511 A1 | 3/2011 | Brannan et al. |
| 2011/0071512 A1 | 3/2011 | Behnke, II et al. |
| 2011/0071582 A1 | 3/2011 | Willyard et al. |
| 2011/0073594 A1 | 3/2011 | Bonn |
| 2011/0077632 A1 | 3/2011 | Rossetto |
| 2011/0077633 A1 | 3/2011 | Bonn et al. |
| 2011/0077634 A1 | 3/2011 | Brannan |
| 2011/0077635 A1 | 3/2011 | Bonn |
| 2011/0077636 A1 | 3/2011 | Brannan et al. |
| 2011/0077637 A1 | 3/2011 | Brannan |
| 2011/0077638 A1 | 3/2011 | Brannan |
| 2011/0077639 A1 | 3/2011 | Brannan et al. |
| 2011/0098695 A1 | 4/2011 | Brannan |
| 2011/0098696 A1 | 4/2011 | Brannan |
| 2011/0098697 A1 | 4/2011 | Brannan |
| 2011/0118721 A1 | 5/2011 | Brannan |
| 2011/0118730 A1 | 5/2011 | DeCarlo |
| 2011/0118731 A1 | 5/2011 | Ladtkow |
| 2011/0152853 A1 | 6/2011 | Manley et al. |
| 2011/0172659 A1 | 7/2011 | Brannan |
| 2011/0184403 A1 | 7/2011 | Brannan |
| 2011/0190630 A1 | 8/2011 | Kim et al. |
| 2011/0190754 A1 | 8/2011 | Kim et al. |
| 2011/0196362 A1 | 8/2011 | Rossetto |
| 2011/0203104 A1 | 8/2011 | Mahajan et al. |
| 2011/0208177 A1 | 8/2011 | Brannan |
| 2011/0208180 A1 | 8/2011 | Brannan |
| 2011/0208184 A1 | 8/2011 | Brannan |
| 2011/0213351 A1 | 9/2011 | Lee et al. |
| 2011/0213352 A1 | 9/2011 | Lee et al. |
| 2011/0213353 A1 | 9/2011 | Lee et al. |
| 2011/0218527 A1 | 9/2011 | Prakash et al. |
| 2011/0224504 A1 | 9/2011 | Ladtkow et al. |
| 2011/0238053 A1 | 9/2011 | Brannan et al. |
| 2011/0238054 A1 | 9/2011 | Kim et al. |
| 2011/0238055 A1 | 9/2011 | Kim et al. |
| 2011/0270240 A1 | 11/2011 | Shiu et al. |
| 2011/0282336 A1 | 11/2011 | Brannan et al. |
| 2011/0295245 A1 | 12/2011 | Willyard et al. |
| 2011/0295246 A1 | 12/2011 | Prakash et al. |
| 2011/0299719 A1 | 12/2011 | Podhajsky et al. |
| 2011/0299727 A1 | 12/2011 | Podhajsky et al. |
| 2011/0301589 A1 | 12/2011 | Podhajsky et al. |
| 2011/0301590 A1 | 12/2011 | Podhajsky et al. |
| 2011/0301591 A1 | 12/2011 | Podhajsky et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 171 967 | 2/1986 |
| EP | 0 246 350 | 11/1987 |
| EP | 0 310 431 | 4/1989 |
| EP | 0 521 264 | 1/1993 |
| EP | 0 556 705 | 8/1993 |
| EP | 0 558 429 | 9/1993 |
| EP | 0 608 609 | 8/1994 |
| EP | 0 836 868 | 4/1998 |
| EP | 0 882 955 | 12/1998 |
| EP | 1 070 518 | 1/2001 |
| EP | 1 159 926 | 5/2001 |
| EP | 0 648 515 | 4/2003 |
| EP | 1 465 037 | 10/2004 |
| EP | 1 645 234 | 4/2006 |
| EP | 1 656 900 | 5/2006 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |

| | | |
|---|---|---|
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| GB | 2 434 872 | 8/2007 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO93/24066 | 12/1993 |
| WO | WO94/28809 | 12/1994 |
| WO | WO96/04860 | 2/1996 |
| WO | WO97/06739 | 2/1996 |
| WO | WO96/18349 | 6/1996 |
| WO | WO96/29946 | 10/1996 |
| WO | WO96/34571 | 11/1996 |
| WO | WO96/39914 | 12/1996 |
| WO | WO97/06740 | 2/1997 |
| WO | WO97/06855 | 2/1997 |
| WO | WO97/17029 | 5/1997 |
| WO | WO99/01074 | 1/1999 |
| WO | WO99/04710 | 2/1999 |
| WO | WO99/22657 | 5/1999 |
| WO | WO00/67846 | 11/2000 |
| WO | WO01/00114 | 1/2001 |
| WO | WO2004/045436 | 6/2004 |
| WO | WO2004/047659 | 6/2004 |
| WO | WO2005/009528 | 2/2005 |
| WO | WO2005/115235 | 12/2005 |
| WO | WO2006/068430 | 6/2006 |
| WO | WO2008/043999 | 4/2008 |
| WO | WO2008/044013 | 4/2008 |
| WO | WO2008/071914 | 6/2008 |
| WO | WO2008/110756 | 9/2008 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non•LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-lridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1993.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1974, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report Ep 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.

European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report for European Application No. 10181599.1 dated Jun. 14, 2012.

* cited by examiner

ELECTROSURGICAL SYSTEM EMPLOYING MULTIPLE ELECTRODES

CROSS REFERENCE TO RELATED APPLICATION

The present application is a continuation of U.S. Utility application Ser. No. 12/748,582 filed on Mar. 29, 2010 by David Heard et al., now U.S. Pat. No. 8,062,290, which is a continuation of U.S. Utility application Ser. No. 12/201,291 filed on Aug. 29, 2008 by David Heard et al., now U.S. Pat. No. 7,699,842, which is a continuation of U.S. Utility application Ser. No. 11/242,391 filed on Oct. 3, 2005 by David Heard et al., now U.S. Pat. No. 7,553,309, which claims priority to U.S. Provisional Application Ser. No. 60/616,971 filed on Oct. 8, 2004 by David Heard et al. The entire contents of each of the above-referenced applications are incorporated by reference herein.

BACKGROUND

1. Technical Field

The present disclosure is directed to electrosurgical systems, and, in particular, to a radiofrequency electrosurgical system employing multiple electrodes for producing large ablation volumes in tissue or producing multiple ablation volumes in tissue during a single procedure.

2. Description of the Related Art

The use of radiofrequency electrodes for ablation of tissue in a patient's body is known. In a typical situation, a radiofrequency electrode comprising an elongated, cylindrical shaft with a portion of its external surface insulated is inserted into the patient's body. The electrode typically has an exposed conductive tip, which is used to contact body tissue in the region where the heat lesion or ablation is desired. The electrode is connected to a radiofrequency power source, which provides radiofrequency voltage to the electrode, which transmits the radiofrequency current into the tissue near its exposed conductive tip. This current usually returns to the power source through a reference electrode, e.g., a return electrode, which may comprise a large area conductive contact connected to an external portion of the patient's body. This configuration has been described in articles, as for example, a research paper by Cosman, et al., entitled "Theoretical Aspects of Radiofrequency Lesions in the Dorsal Root Entry Zone," Neurosurgery, December 1984, Vol. 15, No. 6, pp 945-950, and a research paper by Goldberg, et al. entitled "Tissue Ablation with Radiofrequency: Effective Probe Size, Gauge, Duration, and Temperature and Lesion Volume" Acad Radio., 1995, Vol. 2, No. 5, pp 399-404. Radiofrequency lesion generators and electrode systems such as those described above are commercially available from Valleylab, located in Boulder, Colo.

To enlarge ablation volumes, electrodes with curved conductive tips have been proposed. Such tips are injected from a cylindrical electrode placed near the targeted or desired tissue volume to produce an off-axis, curved arc within the targeted or desired tissue. In this way, off-axis ablation volumes may be produced away from the central axis of the inserted cannula. The off-axis lesions produced by these off-axis radiofrequency electrodes enlarge the lesion volume away from an axially symmetric, exposed electrode tip. One example of this type of an off-axis electrode is the Zervas Hypophysectomy Electrode available from the company Radionics, Inc., located in Burlington, Mass. Another example of this type of an off-axis electrode is the multiple side-emitting, off-axis electrode made by Radiotherapeutics, located in Mountainview, Calif. The multiple electrode elements range in curved arcs at various azimuthal angles. By making an umbrella of off-axis tip extensions at various azimuthal angles relative to a central insertion cannula, an enlarged lesion volume can be produced. Disadvantages of irregular heat ablation shapes and large central cannula sizes are discussed below.

Also, pairs of electrodes have been inserted into the body in a bipolar configuration, typically in parallel pairs held close to each other. Examples of such bipolar configurations are available from the company Elekta AB, located in Stockholm, Sweden. In such bipolar configurations, one electrode serves as a source and the other serves as a sink for the radiofrequency current from the radiofrequency generator. In other words, one electrode is disposed at the opposite voltage (pole) to the other so that current from the radiofrequency generator is drawn directly from one electrode to the other. The primary purpose of a bipolar electrode arrangement is to insure more localized and smaller heat ablation volumes. With such configurations, the ablation volume is restricted to the region between the bipolar electrodes.

Hyperthermia is a method of heating tissue, which contains a cancerous tumor, to thermally non-lethal levels, typically less than 45 degrees Centigrade combined with irradiation of the tissue with X-rays. Such application of mild non-lethal heating in combination with radiation by X-rays enhances destruction of cancer cells while sparing the normal cells from being killed. For hyperthermia, multiple arrays of high frequency electrodes are implanted in tumors. The electrodes are typically placed in a dispersed fashion throughout the tumor volume to cover the tumor volume with uniform heat, which is below the lethal 45 degree level. The electrodes are sequentially applied with high frequency voltage so that each electrode heats in sequence its neighborhood tissue and then shuts off. Then, the next electrode does the same in a time series. This sequence of cycling the voltage through the electrodes continues at a prescribed frequency and for a time period ranging anywhere from minutes to hours. The primary objective of hyperthermia is not to fully ablate tumors by outright heat destruction of the cancerous tumor. On the contrary, its objective is to avoid temperatures above 45 degrees C. anywhere in the treatment volume. The article by Melvin A. Astrahan entitled "A Localized Current Field Hyperthermia System for Use with 192-Iridium Interstitial Implants," in Medical Physics, 9(3), May/June 1982, describes the technique of radiofrequency hyperthermia.

Electrodes with cooled conductive tips have been proposed by Goldberg, et al., in their article referenced above. With cooling, electrode tips generally produce larger lesion volumes with radiofrequency electrodes, which are not cooled.

The electrode systems discussed above are limited by the practical size of lesion volumes they produce. For example, standard single cylindrical electrodes, with cool tips, as described above, make lesion volumes up to 3 to 4 cm in diameter in living tissue such as the liver using cannulae of 1 to 2 mm in diameter and several centimeters exposed tip length. The umbrella lesions made by multiple side-emerging, exposed tips, also produce lesion sizes of 3 to 4 cm volume diameter. A severe hazard of multiple extrusion of side-outlet electrodes is that it produces hemorrhaging by the multiple passes of the side outlet electrodes near the central cannula. Also, at the periphery of such side-emitting electrode lesions, irregularities and undulations in lesion shape and inhomogeneities in temperature around the side-emitted electrode tips produce hot and cold spots over the lesion volume. These may cause focal boiling and charring of tissue with unpredictable and dangerous consequences. For example, consider a large tumor of about 3 to 4 cm diameter in the liver. In such an example, there is a further risk that such undulations and variations in the shape of the periphery of the heat ablation zone would cause portions of the cancerous tumor to be missed by the heat ablation, which of course, would result in continued tumor growth and progression of cancer. Further, a single central cannula, which has one or many side-emitting radiofrequency electrode tips has a diameter, which increases with the number of radiofrequency tips that emerge from it. When the diameter reaches 3 to 4 mm for such a central cannula, there is the disadvantage of increased risk of hemorrhage and/or great pain or discomfort to the patient during insertion of the large central cannula into the tissue.

Thus, a configuration of radiofrequency electrodes which can accomplish ablation volumes in the range of 4 to 6 cm diameter or greater for the purpose of adequately treating large cancerous tumors in the body is necessary to effectively destroy the tumor and combat cancerous cells from spreading. It is further necessary that such an electrode system involve a simple geometry, reduced numbers of tissue insertions, simple planning of needle placement, and simple planning of heat ablation geometry and distribution. Furthermore, an electrode system is desired which can be easily inserted into an organ or through the skin with minimal risk of hemorrhage and discomfort to the patient. An electrode system and method, which produces minimal lesion inhomogeneities to avoid complications of boiling and charring, and which avoids the inadvertent missing of outlying colonies of cancer cells in an irregular tumor is not only desirable, but necessary.

SUMMARY

The present disclosure relates to a radiofrequency electrosurgical system that employs multiple electrodes for producing large ablation volumes in tissue or producing multiple ablation volumes during a single procedure. By employing multiple electrodes in a single procedure, the electrosurgical system can create large lesions (~6 cm or greater in diameter) or can ablate 2 or more separate lesions simultaneously. The electrosurgical system of the present disclosure allows for the use of multiple small-diameter electrodes instead of a single large-diameter electrode which minimizes the risk of hemorrhaging. Further, by employing multiple electrodes, the electrosurgical system can ablate volumes of various shapes and sizes.

The present disclosure includes a system for heat ablation of tissue in which energy is sequentially applied to at least two electrodes inserted into tissue. The system includes a radiofrequency source configured to supply radiofrequency energy to two or more electrodes for treating tissue, one or more return electrodes and a controller. The return electrode is configured to return the radiofrequency energy to the radiofrequency source. The controller is configured to sequentially apply the radiofrequency energy to each of the electrodes for a pre-determinable period of time, wherein the pre-determinable period of time is determined by a surgical procedure or the number of electrodes. The controller further includes a determiner configured to determine an off time for the next electrodes in sequence and a comparator to compare to compare the off time for the next electrode in sequence to a predetermined minimum off time. The controller applies the radiofrequency energy to the next electrode in sequence when the off time is greater than the predetermined minimum off time.

The system may further include current and voltage measuring circuitry operably connected to at least one of the at least two electrodes. An impedance of an electrode may be calculated based on the measured current and voltage.

The system may also include an internal load and circuitry configured to switch the RF energy to the internal load. The radiofrequency energy may be switched to the internal load when the off time is less than the predetermined minimum off time.

The system may also include circuitry that restricts the flow of radiofrequency energy to an electrode when the calculated impedance exceeds a threshold impedance. The circuitry may allow the flow of radiofrequency energy to an electrode when the calculated impedance does not exceed a threshold impedance. The threshold impedance may be related to a baseline impedance and/or a predetermined differential impedance. The baseline impedance may include the lowest calculated impedance obtained in the initial seconds of radiofrequency energy delivery. Alternatively, the baseline impedance may be the lowest average of consecutive calculated impedances obtained during the initial 30 seconds of radiofrequency energy delivery.

The predetermined differential impedance may be about 30 ohms if the baseline impedance is less than about 100 ohms. Alternatively, the predetermined differential impedance may be about 30% of the baseline impedance if the baseline is greater than 100 ohms.

The system may further include circuitry to sequence the delivery of radiofrequency energy between the electrodes, wherein electrodes are skipped if the calculated impedance is above a predetermined threshold.

The system may further include an internal load and circuitry configured to direct the radiofrequency energy to the internal load. The radiofrequency energy may be simultaneously delivered to the internal load and one of the electrodes.

In yet another embodiment, the system may further include circuitry to measure current to at least one of the electrodes and the controller reduces the duty cycle if the measured current exceeds a predetermined current limit. The predetermined current limit may be about 2 amps.

In yet another embodiment, the system may include temperature measuring circuitry electrically coupled to an electrode. The energy applied to a first electrode is switched to a next electrode when the temperature at the first electrode is greater than a predetermined temperature.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure will be described herein below with reference to the accompanying drawings. In the following description, well-known functions or constructions are not described in detail to avoid obscuring the disclosure in unnecessary detail.

Figure 1:
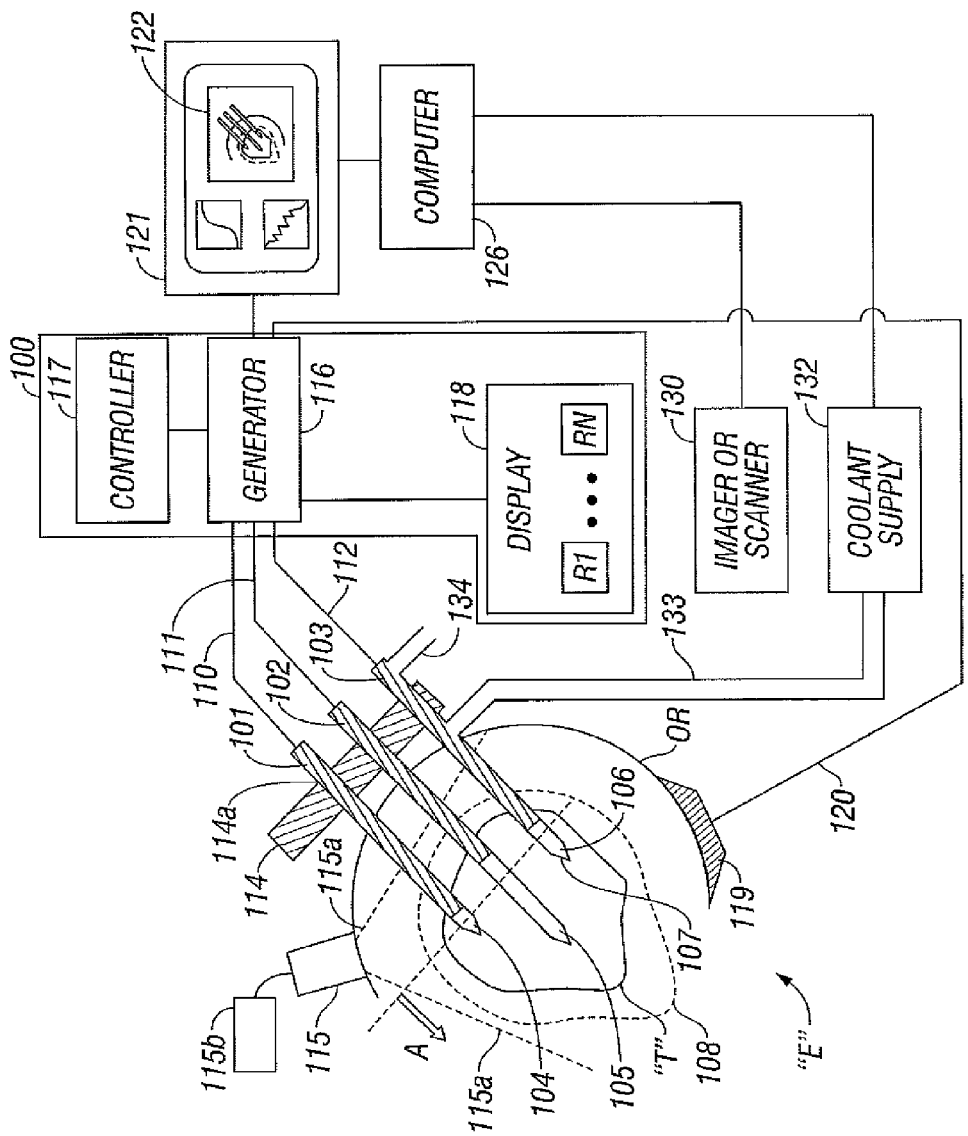
FIG. 1 shows schematically multiple radiofrequency electrodes positioned in a patient's organ for producing heat ablation of a targeted tissue area in accordance with an electrosurgical system of the present disclosure.

Referring now to FIG. 1, one embodiment of the electrosurgical system using multiple electrodes in accordance with the present disclosure referenced by letter E is generally illustrated. The electrosurgical system E comprises a plurality of electrodes 101, 102, and 103, that are inserted into an organ OR, which may represent any organ in a human body. Their distal tips 104, 105, and 106, respectively, are uninsulated and conductively exposed so that electrical currents induce heating within the tissue or organ OR. A targeted volume of tissue T is shown in sectional view, which may represent, for example, a tumor or other abnormality in a human body.

The electrodes 101, 102, and 103, are individually coupled by wires or cables 110, 111, and 112, as shown, to a generator 100. The generator 100 will include a radiofrequency or high frequency type of generator 116 for generating electrosurgical energy to be applied to the organ. The generator 100 has control elements, e.g., a controller, illustrated generally by block 117, which may, for example, switch radiofrequency power sequentially to each of the electrodes, increase the radiofrequency power output to the electrodes, control temperature when the electrodes or satellite sensors comprise temperature sensors, monitor or control impedance, power, current, voltage, or other output parameters. The generator 100 may include a display provision, illustrated by block 18, within it or as a separate system, for providing a display of heating parameters such as temperature for one or more of the electrodes, impedance, power, current, or voltage of the radiofrequency output. Such individual display readings are illustrated by the reference letters R1, . . . to RN and will generally correspond to the number of electrodes associated with the system.

It is to be appreciated that the energy source 116, the controller 117 and display 118 may be disposed in a single housing or implemented as separate components. For example, in one embodiment, the controller 117 may be a separate component adapted for receiving a single constant voltage from a energy source wherein the controller varies parameters of the energy to obtain a desired output.

A reference electrode 119, e.g., a return electrode, is also shown, which may be placed in contact with the skin of a patient or the external surface of the organ OR with a connection 120 to the generator 100. In one embodiment, this serves as a path for return current from the generator 100 through the electrodes 101, 102 and 103.

The electrodes 101, 102 and 103 in accordance with one exemplary embodiment, comprise rigid shafts, which may be easily urged into the body tissue. They terminate in tissue-penetrating pointed tips 107 on electrode ends 106. They have a portion of their external shaft surface of insulated material indicated by the hatched line areas on electrodes 101, 102 and 103. The distal tip referenced by 104, 105, and 106 for each electrode comprise conductive metal and are connected through the shafts 101, 102 and 103 to the connection cable 110, 111, and 112 respectively, and thereby to the generator output source 100.

According to the present disclosure and illustrated in FIG. 1, the electrodes 101, 102 and 103 may be placed in a single target, e.g., a tumor. The heating effect of the multiple electrodes is similar to that accomplished by one large single electrode. The individual electrodes 101, 102 and 103 cause less trauma and do not induce hemorrhaging when they penetrate the organ OR because of their smaller size. Yet when they are connected to a radiofrequency voltage source, they represent an effectively much larger electrode. In this way, larger heat volumes, and therefore ablation sizes, may be achieved.

As an illustration, in FIG. 1 the targeted volume is represented in sectional view by the line T. Consider that it is desired to ablate the targeted region T by fully engulfing it in a volume of lethal heat elevation. The targeted area T may be, for example, a tumor which has been detected by image scanner 130. CT, MRI, or ultrasonic image scanners may be used, and the image data transferred to computer 126. As an alternate example, an ultrasonic scanner head 115 may be disposed in contact with OR to provide an image illustrated by lines 115A. Data processor 115B may be connected to display devices to visualize the tumor T and/or ablation zone 108 in real time during the ablation procedure. The image representation of the scan may be displayed on display unit 121, which may, for example, be a CRT screen. Slice renderings through the organ OR may be displayed in window 122 to represent the size and position of targeted volume T. Placement of the electrodes 101, 102 and 103 may be predetermined based on such image data as interactively determined by real-time scanning of organ OR. The electrodes may be inserted into the tissue by freehand technique by a guide block with multiple hole templates, or by stereotactic frame or frameless guidance. A stereotactic guide is shown schematically by element 114. Guide holes such as 114A for electrode 101 aim it to the desired targeted position based on image data.

In accordance with the present disclosure, electrodes 101, 102 and 103 are independently activated with radiofrequency energy from generator 100. They thus will act as an effectively larger electrode. Their relative positions and orientations enable different positive shapes and sizes of ablation volumes to be made than could possibly be made from a single larger electrode. For example, in FIG. 1 the dashed line represents the ablation isotherm in a sectional view through organ OR. Such an ablation isotherm may be the surface achieving temperatures of approximately 50 degrees or greater. At that temperature range, sustained for about 30 seconds to several minutes, tissue cells will be killed or ablated, in accordance with the paper of Cosman, et al., referred to above. The shape and size of the ablation volume illustrated by dashed line 108 may accordingly be controlled by the configuration and/or placement of the individual electrodes, the geometry of the exposed tips 104, 105, and 106, the amount of radiofrequency power applied, the time duration that the power is applied, cooling of the electrodes, and so on.

In each of the examples, also, the electrodes may be cooled by a coolant, such as chilled circulating saline, within them. A coolant supply 132 will supply coolant to the electrode via connection 133, e.g., tubing. The coolant will circulate among the electrodes and either return to the coolant supply or be discharged via connection 134. Such electrodes are described in U.S. Pat. No. 6,506,189 entitled "COOL-TIP ELECTRODE THERMOSURGERY SYSTEM" issued to Rittman, III et al., on Jan. 14, 2003, the contents of which are herein incorporated by reference. Thereby, the multiple electrodes represent an effectively larger, cooled radiofrequency structure. With adaptations a much larger radiofrequency ablation may be accomplished. Multiplicities of cluster electrodes may also be implemented for other geometric or clinical advantages. Cluster electrodes are described in U.S. Pat. No. 6,530,922 entitled "CLUSTER ABLATION ELECTRODE SYSTEM" issued to Cosman et al., on Mar. 11, 2003, the contents of which are herein incorporated by reference.

The use of a multiplicity of N electrodes increases the overall conductive exposed tip area by which to send radiofrequency current for heating into the tissue. This increases the heating power that may be delivered and thus increases the size of the ablation volume possible. Furthermore, the cooling capacity of a multiplicity of N electrodes also increases as the number N increases. Increasing the number of electrodes increases the cooling surface area near the electrodes. Thus, the heat sinking effect from a plurality of electrodes is greater than the heat sinking effect from a single electrode element. This enables the lesion size to be expanded accordingly.

An advantage of a multiplicity of smaller electrodes versus insertion of a single large electrode is that the smaller electrodes will produce less chance of hemorrhage. The arrangement of their geometry may also be tailored to the clinical application. Insertion of several small gauge electrodes is less painful, uncomfortable, and risk-inducing than insertion of one large, equivalent radiofrequency electrode. For example, insertion of a cluster of several 18 gauge or 1.25 mm diameter pointed radiofrequency electrodes into the liver produces very low risk of hemorrhage and low discomfort. Insertion of an equivalent, but much larger single electrode, which may have a diameter of, for example, 0.25" or 6.4 mm, would have a higher risk of hemorrhage and would be very uncomfortable for the patient if the electrode were inserted percutaneously.

Figure 2:
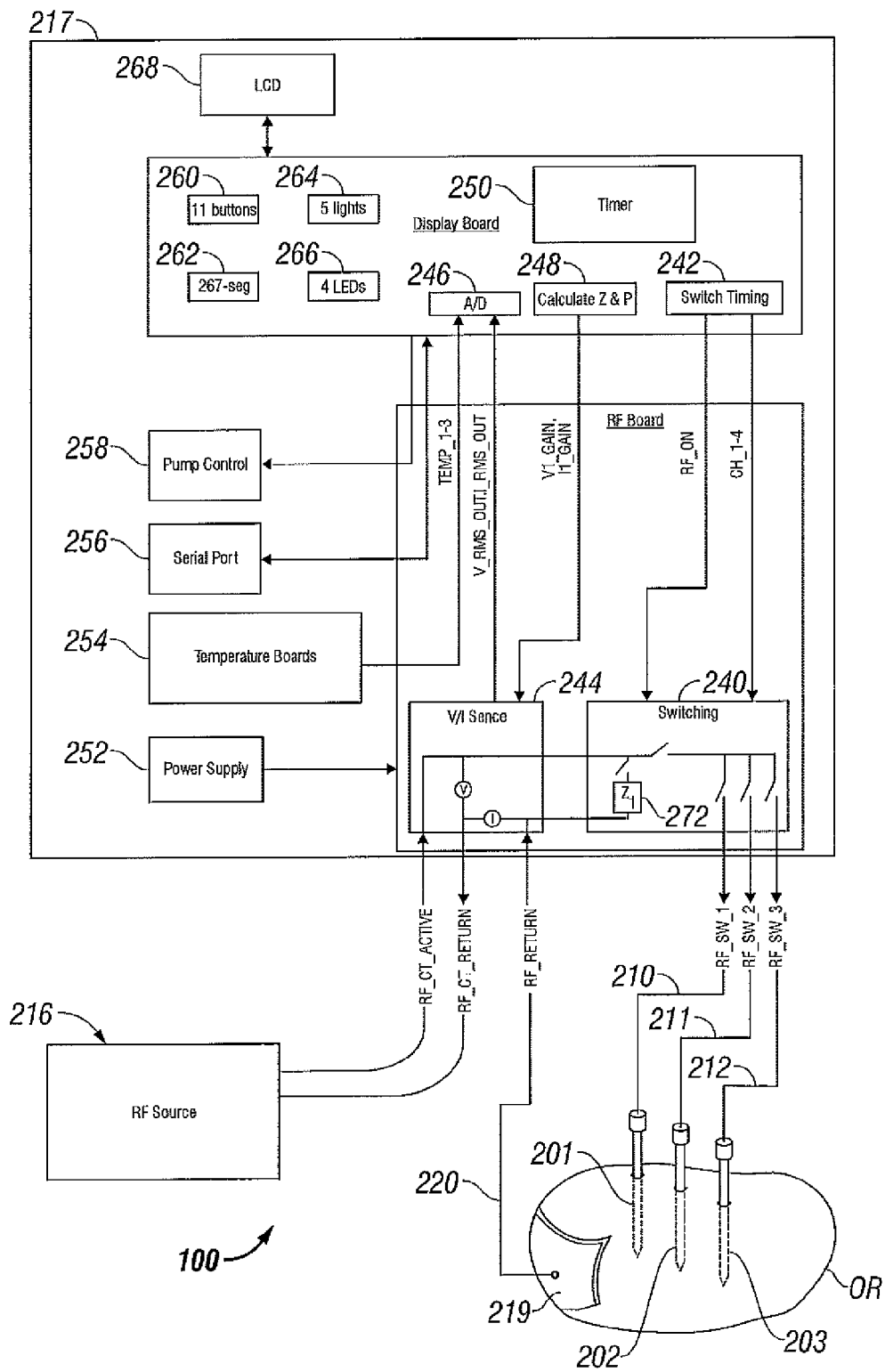
FIG. 2 is a schematic diagram of a electrosurgical generator in accordance with the present disclosure.

Referring to FIG. 2, a schematic diagram of generator 100 of the present disclosure is shown. The generator 100 includes a radiofrequency source 216 for supplying radiofrequency energy and a controller 217 for controlling the supply of radiofrequency energy to the multiple electrodes, the operation of the coolant supply and for the display and entry of control parameters. By way of one example, the radiofrequency source 216 may be a radiofrequency generator with frequency between about 100 kilo Hertz to several hundred mega Hertz. An example of such a generator is the lesion generator available from Valleylab of Boulder, Colo. It may have power output ranging from several watts to several hundred watts, depending on the clinical application.

The controller 217 includes a switching mechanism 240 including a plurality of output channels RF_SW_1, RF_SW_2, RF_SW_3 for individually supplying radiofrequency energy to the multiple electrodes 201, 202, 203. The switching mechanism 240 further includes an internal load 272 for dissipating radiofrequency energy in certain situations when any of the plurality of electrodes can not be activated. Control of the switching mechanism is provided by switch timing circuit 242 which is programmed with executable instructions for switching the radiofrequency energy output among the plurality of channels or the internal load, the sequence of which will be described in detail below in relation to FIGS. 4 and 4A.

The controller 217 further includes V/I sense circuitry 244 for providing the radiofrequency energy from the radiofrequency source 216 to the switching mechanism 240 and for measuring the current and voltage supplied to an active electrode of the multiple electrodes. The V/I sense circuitry 244 will send the measured values of current and voltage, e.g., I_RMS_OUT, V_RMS_OUT, to module 246 which may be a analog-to-digital converter. The digital values of the current and voltage will then be sent to module 248 to calculate impedance and power at the active electrode, which will further be used for controlling the radiofrequency energy output as will be described below.

Timer 250 will be employed to measure the duration of radiofrequency output activation for each channel and to measure a total procedure time.

The controller 217 will further include power supply 252 for supplying power to the various components of the controller 217; at least one temperature board 254 for determining a temperature at a tip of an electrode when the electrode includes a temperature sensor such as a thermocouple; a serial port 256 for coupling the controller 217 to a computer for downloading values from the controller 217 or for reprogramming the controller 217; and a pump control mechanism 258, e.g., a relay, for controlling flow from a coolant supply when a cool-tip electrode is employed. Furthermore, the controller 217 includes a plurality of input and output devices 260, 262, 264, 266, 268 for entering parameters relating to a predetermined procedure and for displaying values measured during the procedure, for example, temperature, current, voltage, procedure time, etc.

A series E(N) of N electrodes 201, 202, 203 is shown inserted into organ or bodily element OR and coupled to the switching mechanism 240. These electrodes may be, for example, metal shafts with an insulated portion, except for an exposed distal tip, as described above. They may have self-penetrating or tissue-piercing, pointed tips. The individual electrodes may or may not have pointed tissue-piercing tips, as the clinical need and technique requires. For example, in the brain, a rounded, smooth-tipped electrode will penetrate brain tissue and could provide less risk of hemorrhage from penetrating blood vessels. For percutaneous insertion, pointed electrodes or pointed guide cannulae followed by round-tipped electrodes may suit the clinical technique.

Each electrode 201, 202, 203 is individually coupled, via cables 210, 211, 212 respectively, to an output channel of switching mechanism 240. A reference area electrode 219 is shown contacting a surface of the organ OR. It is connected by element 220 to the controller 217 which may act to return radiofrequency current to the power generator 216 or cooling fluid if area electrode 219 is also a cooled type.

Such a configuration may be clinically useful if a large volume or block of tissue is to be ablated. For example, if the electrodes 201, 202, 203 are inserted in a nearly parallel array in an organ such as the liver, and a reference electrode such as 219 is a plate electrode placed on the surface of the liver roughly parallel to the electrode array E(N), then an effectively "parallel plate" electrode configuration is achieved. In that case, a relatively uniform and large block of ablative heating volume may be induced between the electrode array E(N) and the plate electrode 219. Within that volume, a cancerous tumor or other tissue abnormality, which is desired to be ablated, would be completely destroyed. Variations in electrode placement and geometry, such as parallel or non-parallel, may be used to create changes in shape of the ablation volume as clinical needs require. Electrode insertion from varied directions may help in avoiding critical anatomical structures or obstructions while still increasing the number of electrode elements to achieve the desired lesion size. Variations in the degree of exposed conductive tip for electrode elements may vary according to a clinical targeted site.

Figure 3:
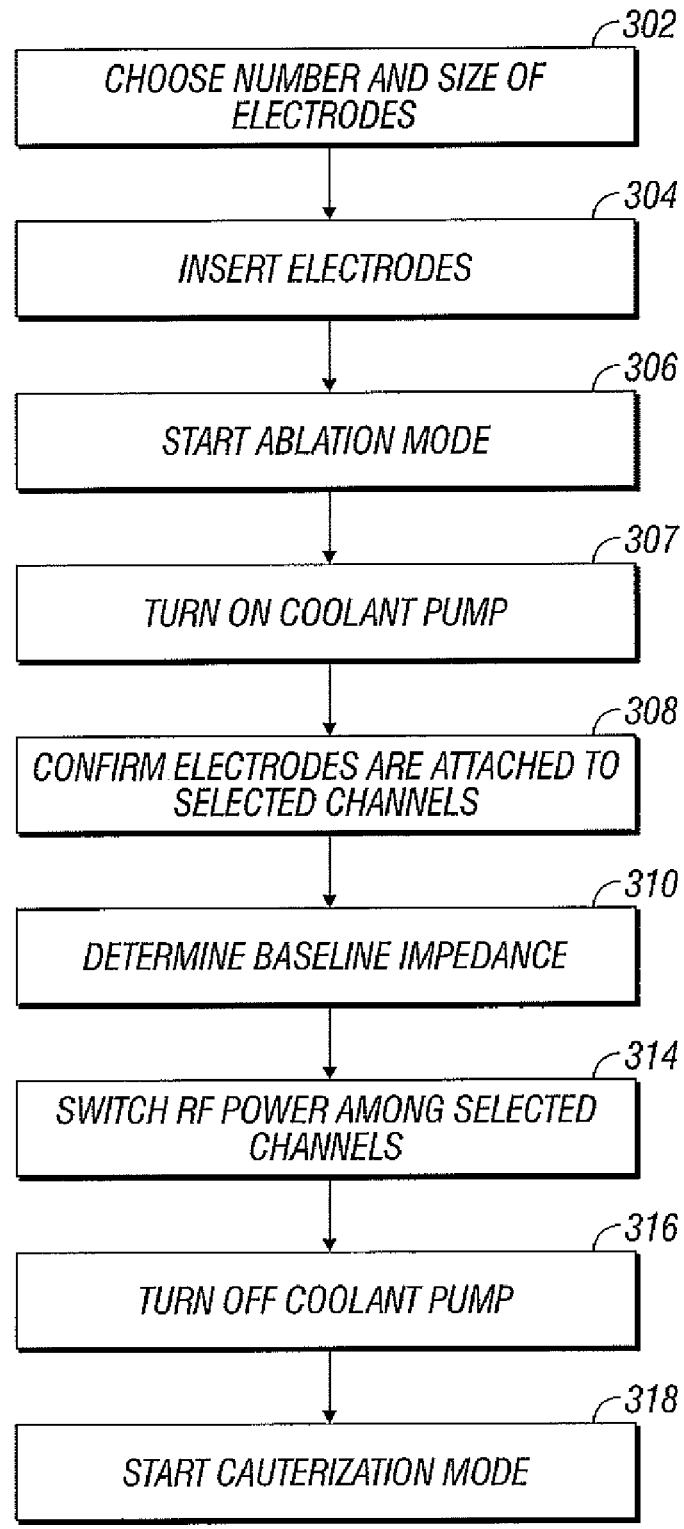
FIG. 3 is a flowchart illustrating an operation of the electrosurgical system.

FIG. 3 illustrates an operation of the electrosurgical system using multiple electrodes, as shown in FIG. 2, in accordance with one embodiment of the present disclosure. At the outset, depending on the clinical conditions or requirements, an appropriate or desired configuration of the multiple electrodes is selected by the clinician (step 302). At this stage, determinations as to the following factors are considered by the clinician, which are provided by way of example: (a) the number of electrodes; (b) their relative geometry, individual electrode sizes and tip exposures; (c) whether the electrodes are desired in one predetermined cluster or individual sizes and configurations for individual placement within the organ; (d) the determination whether cooled or non-cooled electrodes are desired. Step 302 may also represent the steps of processing image scan data from a CT, MR, ultrasound, or other type of scanner to determine the position of a targeted volume such as a tumor within the patient's body and the desired approach, placement, size, and number of electrodes. This may be done on a computer graphic workstation using 3D graphics and stereotactic orientation and methods, as illustrated by the XKnife, StereoPlan, or XSeed treatment planning systems of Radionics, Inc., of Burlington, Mass.

The stereotactic positioning of the multiple electrodes may be preplanned on the workstation. The heat isotherms and ablation volume and time-course of the ablation may be calculated and displayed on the workstation as part of the preplan. Based on historical or empirical information, the clinician may in step 302 determine the desired power to be delivered to the tissue, the temperature as measured by the electrode or measured elsewhere in the tissue by satellite temperature-sensing electrodes, the desired time duration of radiofrequency heating, and the characteristics of impedance, to determine cut-offs and control against boiling, charring, and other untoward effects. This may be done as a preplan using 3D computer graphics of the entire heating process.

The step of inserting the multiple electrodes is represented by step 304 in FIG. 3. The electrodes may be placed individually or in unison within the body tissue, as described above. Real-time imaging may be utilized, such as ultrasound, MRI, or CT, during placement of the electrodes to determine their proper position within a targeted volume of tissue. The electrodes are inserted to a desired depth during this step.

In step 306, the clinician will select the ablation mode and the procedure timer will be set to zero. In step 307, the controller 217 will activate pump control 258 to provide cooling to the electrodes. The electrodes can be "piped" in series in that coolant flows from the coolant supply through the first electrode to the second electrode and to the third electrode; then is either discharged or flows back to the supply. The ablation process will not begin until all selected electrodes are below a predetermined limit, e.g., 20° C. This predetermined temperature limit may be user selectable or selected by the controller based on tissue type, procedure selected, etc.

The controller 217 will sequence power through each selected channel of the switching mechanism 240 to determine if an electrode is attached to the channel (step 308). Here, the controller 217 will apply a pulse of radiofrequency power approximately for about 600 ms to the first selected channel. If the measured impedance is below a predetermined limit, the control mechanism will confirm an electrode is attached and repeat the process for each selected channel.

Next, the controller 217 will determine a baseline impedance for each electrode attached (step 310). The controller 217 will apply power to the first selected channel for approximately 30 seconds and record the lowest impedance value measured in the first 10 seconds as the baseline impedance for that channel. The controller 217 will average every 10 impedance data points during the 10 second period and save the lowest average as the baseline impedance. After 30 seconds, the controller 217 will move to the next selected channel and repeat the process to determine the baseline impedance. The controller 217 will move through all selected channels until a baseline impedance is determined for all the channels.

Figure 4:
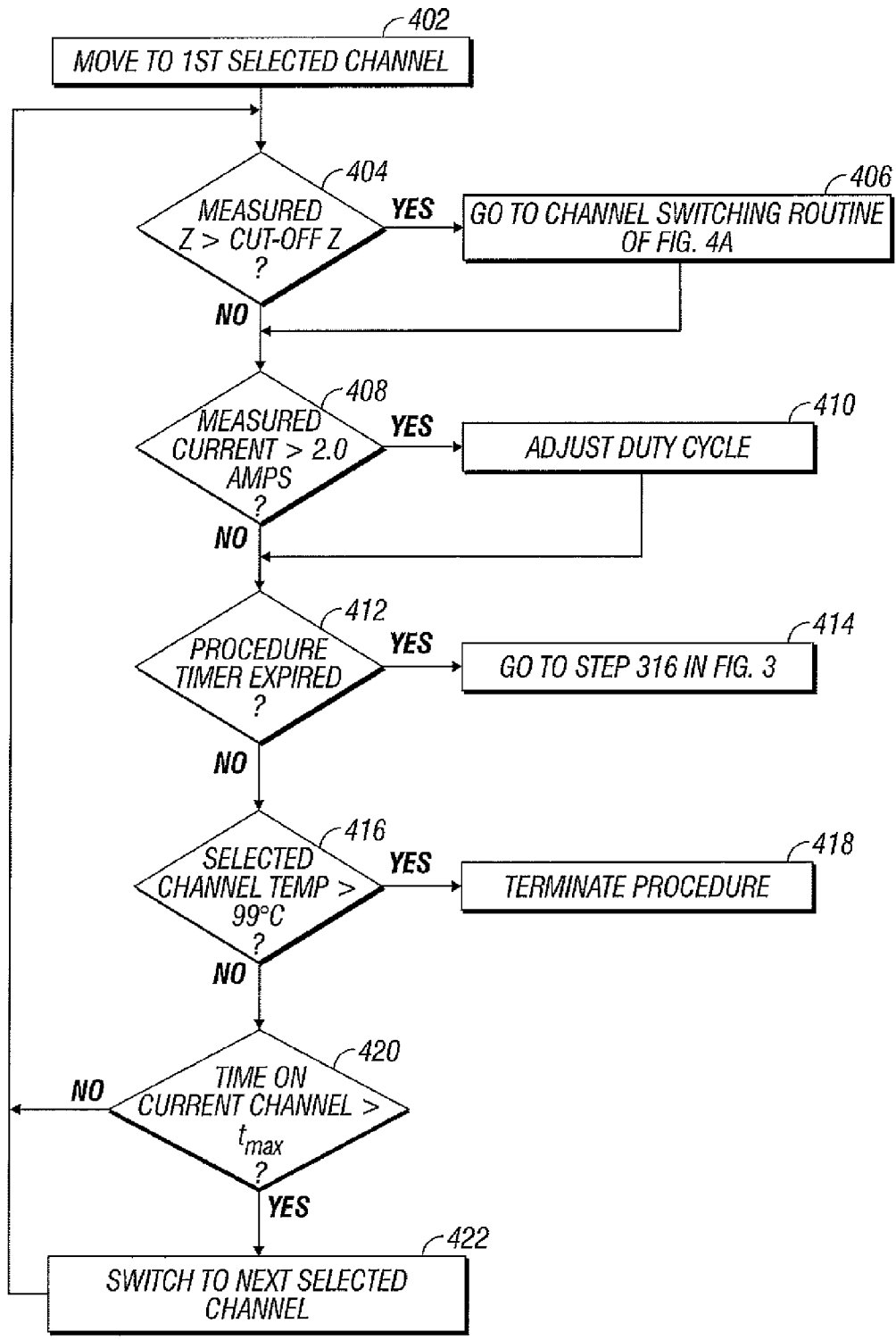
FIG. 4 is a flowchart illustrating an ablation procedure in accordance with the present disclosure.

Once all the selected electrodes are below the predetermined temperature limit, the ablation process will begin and the controller 217 will switch radiofrequency power among the selected channels according to the algorithms illustrated in FIGS. 4 and 4A (step 314). Referring to FIG. 4, the controller 217 will apply power to the first selected channel, e.g., RF_SW_1, to active the first electrode 201 (step 402). Module 248 will determine the impedance at electrode 244 and controller 217 will compare the measured impedance to an impedance cut-off for the selected channel (step 404). The impedance cut-off will be based on the baseline impedance measured for the selected channel. If the baseline impedance is less than 100 ohms, the impedance cut-off will be set at the baseline impedance plus an impedance differential, e.g., 30 ohms. If the baseline impedance is greater than 100 ohms, the impedance cut-off will be set at the baseline impedance plus 30 percent of the measured baseline impedance. If the instantaneous measured impedance at the selected electrode is greater than the cut-off impedance, e.g., an over-impedance condition, the controller 217 will load the channel switching routine to determine if power should be applied to the next channel or to the internal load 272 (step 406).

Figure 4A:
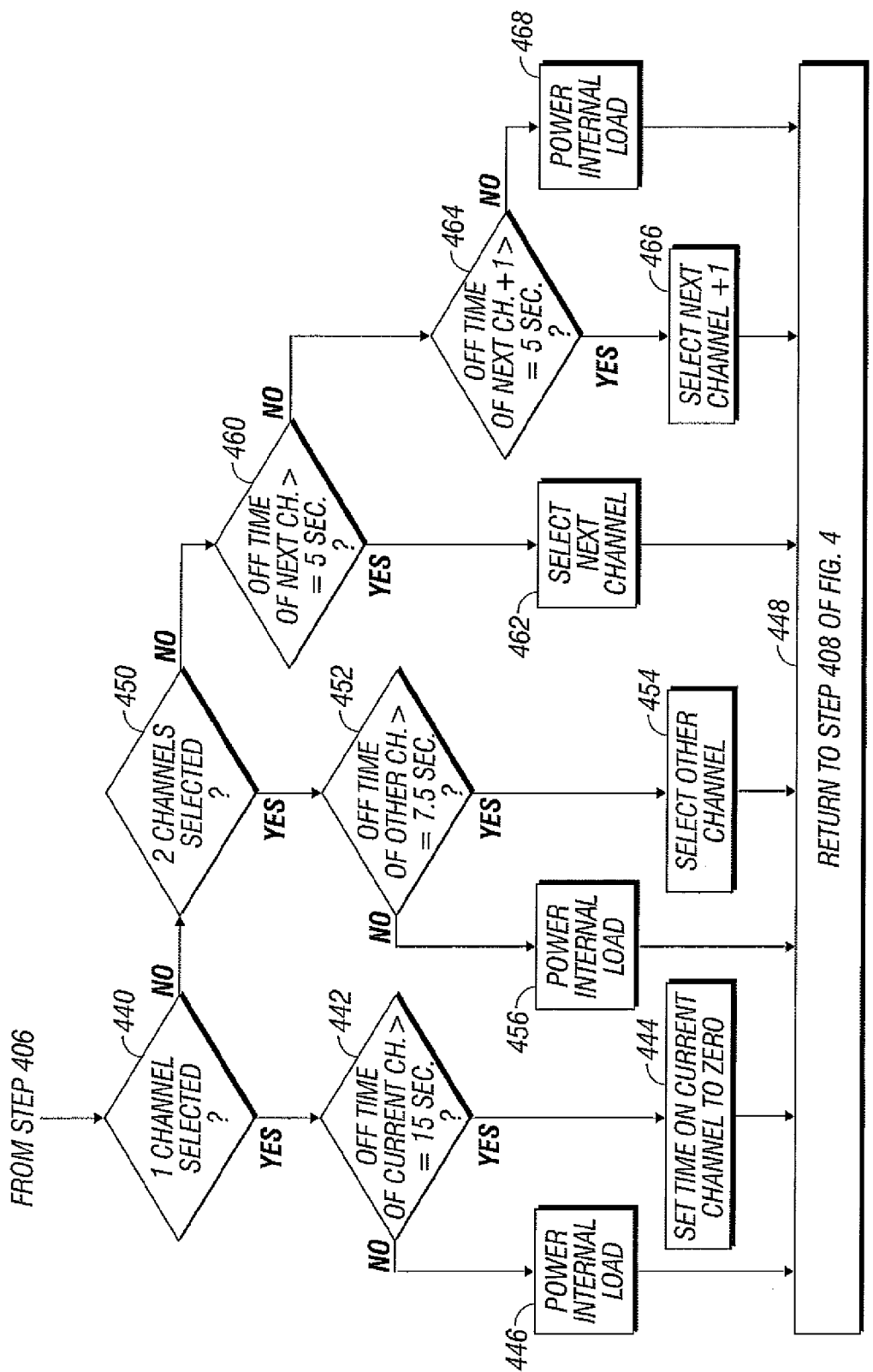
FIG. 4A is a flowchart illustrating a channel switching routine in accordance with the present disclosure.

Referring to FIG. 4A, the switching among electrodes will depend on how many electrodes are selected for the procedure. Each electrode employed in the procedure will have a minimum off time following a period of activation. The minimum off time for each electrode will equal a predetermined period of time, e.g., 15 seconds, divided by the number of selected electrodes. Therefore, in step 440, if one channel is selected for the procedure, the controller 217 will determine if the off time for the current channel is greater than or equal to 15 seconds. If the off time for the current channel is greater than or equal to 15 seconds (step 442), energy will be applied to the current channel selected and the time on for the current channel will be set to zero (step 444) and the process will return to step 408 of FIG. 4. If the off time for current channel is less than 15 seconds, the controller 217 will power the internal load (step 446) and the process will return to step 408 of FIG. 4. If two channels are selected (step 450), the controller 217 will determine if the off time for the other channel is greater than or equal to 7.5 seconds. If the off time for the other channel is greater than or equal to 7.5 seconds (step 452), energy will be applied to the other channel selected (step 454) and the process will return to step 408 of FIG. 4. If the off time for current channel is less than 7.5 seconds, the controller 217 will power the internal load (step 456) and the process will return to step 408 of FIG. 4.

If three channels are selected for the ablation procedure, the controller 217 will determine whether the off time of the next channel in sequence is greater than or equal to 5 seconds (step 460). If the off time for the next channel in sequence is greater than 5 seconds, the controller 217 will select and apply energy to the next channel (step 462) and the process will return to step 408 of FIG. 4. If the off time for the next channel is less than 5 seconds, the controller 217 will determine the off time for the next channel plus one in the sequence of selected channels (step 464). If the off time for the next channel plus one is greater than or equal to 5 seconds (step 464), energy will be applied to the next channel plus one (step 466) and the process will return to step 408 of FIG. 4. If the off time for next channel plus one is less than 5 seconds, the controller 217 will power the internal load (step 468) and the process will return to step 408 of FIG. 4.

In an alternative embodiment, instead of powering the internal load if no channel is available, the generator may stop supplying radiofrequency energy for a predetermined period of time or simply the generator may shut down.

In a further embodiment, when switching from one channel to the next, the internal load may be activated in parallel (or series) with the previously activated channel and remain on until the next channel is activated to avoid the generator from having an open circuit. Prior to removing energy from the current electrode, energy is applied to an internal load. Energy is then removed from the current electrode while maintaining the application of energy to the internal load. Energy is applied to the next electrode before energy is removed from the internal load. A load is continuously applied to the generator where the load is selected from the internal load, an electrode or both the internal load and an electrode.

Referring back to step 404, if the measured impedance at the selected electrode is less than the cut-off impedance, power will continue to be applied. Next, the controller 217 will determine if the current being applied to the selected channel is above a predetermined current limit (step 408). If the current applied to the selected electrode is above the predetermined current limit, e.g., 2 amps, the controller 217 will duty cycle with the internal load to create a 2 amp average (step 410); otherwise, the process will go to step 412. In step 412, the controller 217 will determine if the total procedure time has expired. If the procedure time has expired, the process will return to step 316 of FIG. 3 (step 414) and the ablation process will be complete. If the process time has not expired, the controller 217 will determine if the selected channel temperature has gone above a predetermined temperature limit, e.g., 99° C. (Step 416.) If the selected channel's temperature has gone above the predetermined temperature limit, the selected channel will be turned off and the ablation procedure will be terminated (Step 418). If the temperature of the selected channel is satisfied, the controller 217 will determine if the selected channel has been activated longer than the maximum time allowable for the channel $t_{max}$ (step 420). If the on time exceeds the maximum allowable time, e.g., 30 seconds, the controller 217 will switch to the next selected channel (step 422); otherwise, the process will return to step 404 and process the selected channel again.

In an alternative embodiment, the controller will switch to the next selected channel if the electrode temperature exceeds a predetermined temperature limit, wherein the predetermined temperature limit is less than the predetermined temperature limit in step 416.

Once the procedure time has expired, the ablation of the target volume or volumes should be complete and the process will return to step 316 of FIG. 3. Once the ablation mode is completed, the controller 217 will deactivate pump control 258 and the pump will stop, ceasing the flow of coolant. The clinician will then enter the cauterization mode to remove the electrodes (step 318).

Conventionally, two people are required to cauterized the channel created in the tissue or organ by the insertion of an electrode. One person is required to remove the electrode from the surgical site and a second person is required to control power at the generator to attempt to maintain a predetermined temperature at the tip of the electrode as the electrode is being withdrawn. A method of the present disclosure overcomes the requirement for two people by automatically controlling the temperature of the selected electrode as it is being withdrawn.

Figure 5:
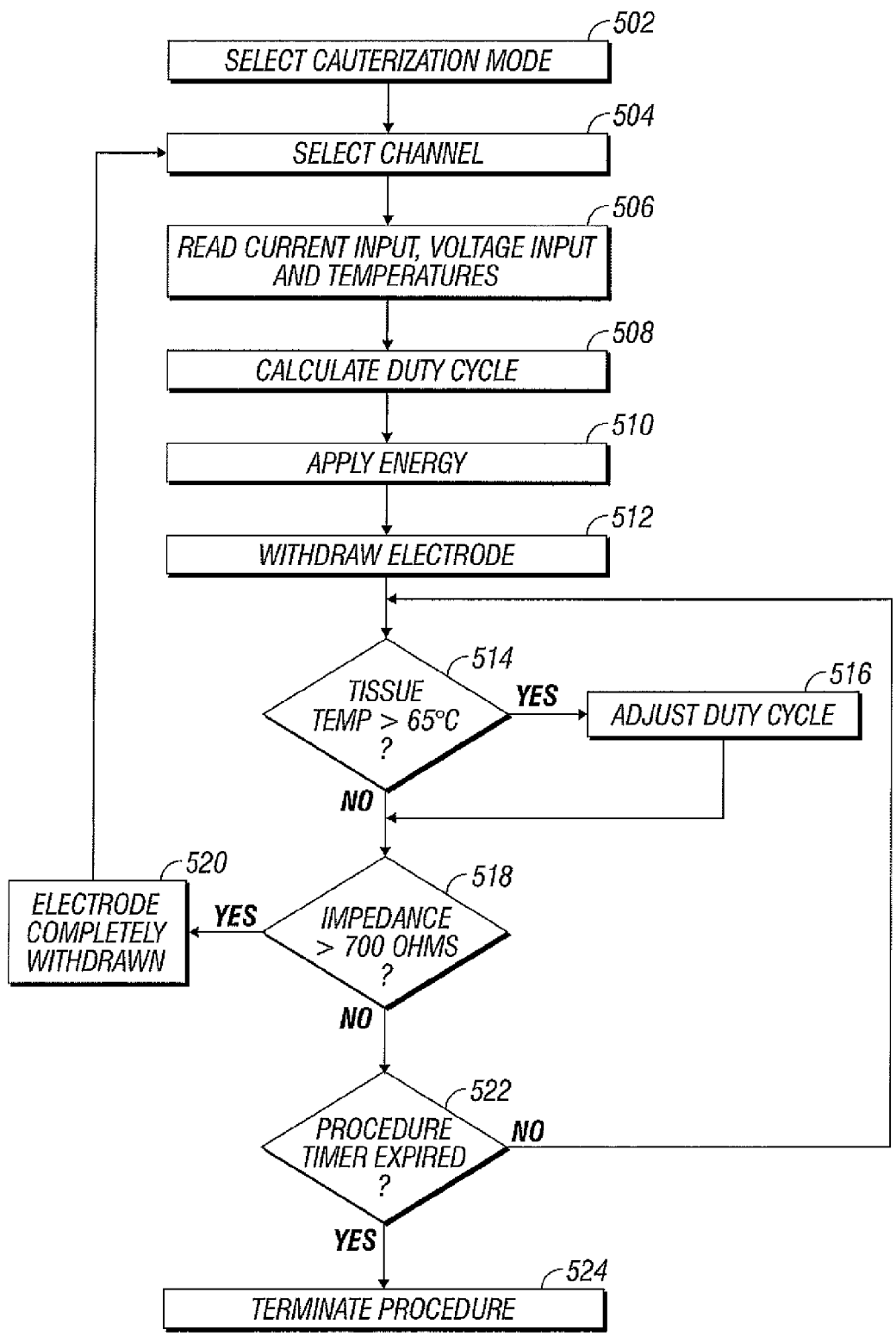
FIG. 5 is a flowchart illustrating a cauterization procedure in accordance with the present disclosure.
Figure 6:
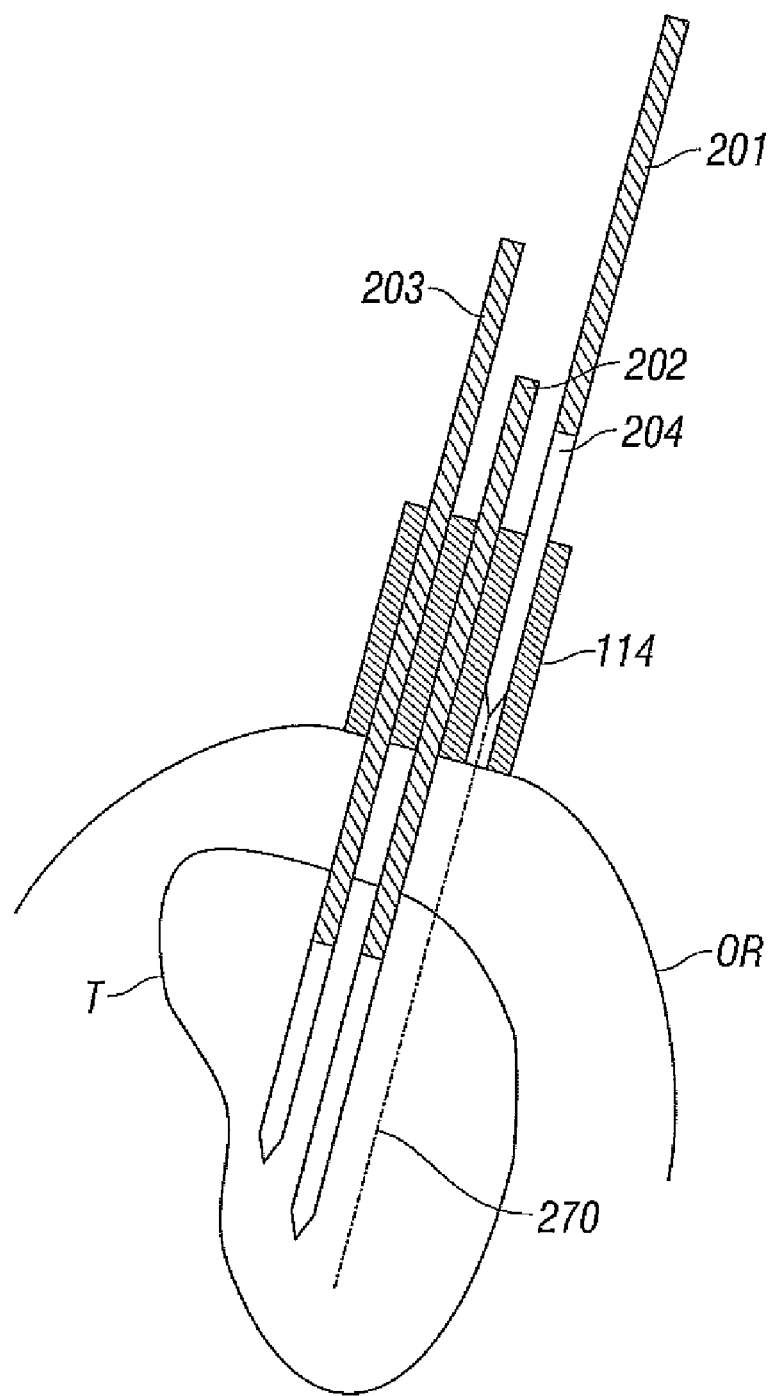
FIG. 6 illustrates a partial sectional view illustrating withdrawal of a single electrode during a cauterization procedure in accordance with the present disclosure.

Referring to FIG. 5, the clinician will enter the cauterization mode (step 502) and select the channel of the electrode to be withdrawn (step 504). In step 506, the controller 217 will read the current, voltage and temperature at the selected electrode. The controller 217 will then calculate the duty cycle (step 508) of the power to be applied to maintain a desired temperature of the exposed portion 204 of the selected electrode 201 as illustrated in FIG. 6. In step 510, power is then applied to the electrode 201 and the clinician will begin to withdraw the electrode (step 512). As the electrode 201 is being withdrawn, power is being applied to cauterize the channel 270 created by the insertion of the electrode 201. During the withdrawal process, the controller 217 will continuously monitor the temperature at the electrode tip 204 to ensure the temperature does not go below a predetermined limit, e.g., 65° C. (step 514). If the temperature at the tip 204 goes above the predetermined limit, the controller 217 will adjust the duty cycle of the radiofrequency energy being applied to maintain the predetermine temperature limit (step 516), e.g., lower the duty cycle. If the temperature at the tip 204 goes below the predetermined temperature limit, the duty cycle will be increased and, subsequently, the controller 217 will monitor the current output to ensure the current supplied is not greater than a predetermined current limit, e.g., 2 amps. If the current output is greater than the predetermined current limit, the duty cycle will be throttled back. Optionally, the predetermined temperature limit may be a range of temperatures of about 60° C. to about 99° C.

The controller 217 will also continuously measure impedance at the electrode (step 518). If the impedance is below a predetermined limit, e.g., 700 ohms, it will be determined that the electrode is still in contact with tissue and the controller 217 will then determine if the procedure timer associated with the selected channel has expired (step 522). If the procedure timer has not expired, the controller 217 will loop back to step 514 to control the power applied to the electrode to maintain the desired temperature. If the controller 217 determines the impedance is greater than the predetermined limit, it will be determined that the electrode is completely withdrawn and the controller 217 will stop applying power to the selected electrode (step 520). Once the electrode is completely withdrawn, the clinician will select the next channel and repeat the process until all electrode are withdrawn from the organ OR. However, if the impedance does not exceed the predetermined limit within the allowable procedure time as determined at step 522, the controller 217 will terminate the cauterization procedure and stop applying power to the selected channel.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A system for heat ablation of tissue in a patient comprising:
a radiofrequency source configured to supply RF energy to at least two electrodes for treating tissue;
at least one return electrode configured to return the RF energy to the radiofrequency source;
a controller configured to determine an off time for each of the at least two electrodes wherein the off time is the amount of time the applied RF energy is off, the controller further configured to sequentially apply the RF energy to each of the at least two electrodes for a pre-determinable period of time, wherein the pre-determinable period of time is determined by a surgical procedure or the number of electrodes; and circuitry configured to switch the RF energy to an internal load,
wherein the controller is further configured to simultaneously apply RF energy to the internal load and one of the at least two electrodes and the controller is configured to apply the RF energy to the next electrode in the sequence when the off time of the next electrode in sequence is greater than a predetermined minimum off time.

2. The system as in claim 1, further comprising:
current and voltage measuring circuitry operably associated with at least one of the at least two electrodes,
wherein the impedance is calculated based on the measured current and voltage.

3. The system as in claim 1,
wherein the circuitry is configured to switch the RF energy to the internal load when the off time for the next electrode in the sequence is less than a predetermined minimum off time.

4. The system as in claim 3, wherein the circuitry is further configured to switch at least a portion of the RF energy to the internal load and a portion of the RF energy to one of the at least two electrodes.

5. The system as in claim 1, wherein the circuitry restricts the flow of RF energy to at least one of the at least two electrodes when a calculated impedance of the at least one of the at least two electrode exceeds a threshold impedance, and
wherein the circuitry allows the flow of RF energy to the at least one of the at least two electrodes when the calculated impedance is less than the threshold impedance
wherein the threshold impedance relates to a baseline impedance and a pre-determined differential impedance.

6. The system as in claim 5, wherein the baseline impedance includes the lowest calculated impedance obtained in the initial 10 seconds of RF energy delivery.

7. The system as in claim 5, wherein the baseline impedance includes the lowest average of consecutive calculated impedances obtained during the initial 30 seconds of operation.

8. The system as in claim 5, wherein the pre-determined differential impedance is 30 ohms if the baseline impedance is less than 100 ohms.

9. The system as in claim 5, wherein the pre-determined differential impedance is 30% of the baseline impedance if the baseline is greater than 100 ohms.

10. The system in claim 5, wherein the circuitry is configured to sequence the delivery of RF energy between the at least two electrodes, wherein an electrode of the at least two electrodes is skipped if the calculated impedance is above a predetermined threshold.

11. The system as in claim 5,
wherein the circuitry is further configured to direct the RF energy to the internal load when the calculated impedance is above a predetermined threshold.

12. The system as in claim 1, further comprising a means to continuously cool an electrode, wherein the means to continuously cool and electrode includes:
a coolant supply that supplies a coolant to at least one of the at least two electrodes via a supply connection; and
a return connection that discharges the coolant from the at least one of the at least two electrodes.

13. The system as in claim 1, further comprising:
current measuring circuitry operably associated with at least one of the at least two electrodes, wherein the controller reduces the duty cycle if a measured current exceeds a predetermined current limit.

14. The system as in claim 13, in which the predetermined current limit is 2 amps.

15. The system as in claim 1, further comprising:
temperature measuring circuitry operably associated with at least one of the at least two electrodes, wherein the applied energy at the energized electrode is switched to the next electrode when the temperature at the energized electrode is greater than a predetermined temperature.

* * * * *